United States Patent [19]

Black

[11] 4,056,529
[45] Nov. 1, 1977

[54] DIBENZOPYRIMIDOAZEPINES

[75] Inventor: Robin Michael Black, Porton, England

[73] Assignee: John Wyeth & Brother Limited, Maidenhead, England

[21] Appl. No.: 647,376

[22] Filed: Jan. 8, 1976

[30] Foreign Application Priority Data

Jan. 16, 1975 United Kingdom .............. 1937/75

[51] Int. Cl.$^2$ ................. C07D 487/04; C07D 223/20; A61K 31/55
[52] U.S. Cl. .......................... 260/251 A; 260/239 D; 260/239.3 T; 424/251
[58] Field of Search .................... 260/251 A, 256.4 F

[56] References Cited

U.S. PATENT DOCUMENTS

| | | | |
|---|---|---|---|
| 3,646,009 | 2/1972 | Winter et al. | 260/239 |
| 3,892,695 | 7/1975 | vander Burg | 260/251 A |

OTHER PUBLICATIONS vander Burg, Eur. J. Clin, Pharmacol, 5(3)166–73, (1973), abstract only supplied.
Nagarajan et al., Indian J. Chemistry, 12, pp. 263–9, Mar. 1974.

*Primary Examiner*—Donald G. Daus
*Assistant Examiner*—Diana G. Rivers

[57] ABSTRACT

The invention relates to dibenzopyrimidoazepines of the formula (I)

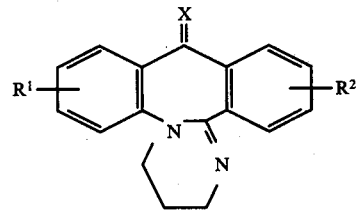

and their acid addition and quaternary ammonium salts. In formula (I) $R^1$ and $R^2$ each represent hydrogen, lower alkyl, lower alkoxy, halogen or trifluoromethyl and X represents two hydrogen atoms, an oxo group, a protected oxo group or an oximino group. The compounds in which X represents two hydrogen atoms, an oxo group or an oximino group possess hypoglycaemic activity. The compound in which X represents a protected oxo group are intermediates for preparing the compounds in which X is an oxo group. The dibenzopyrimidoazepines may be prepared by cyclising or cyclodehydrating novel morphanthridine derivatives.

6 Claims, No Drawings

DIBENZOPYRIMIDOAZEPINES

This invention relates to heterocyclic compounds and more particularly to novel dibenzopyrimidoazepines, to processes for preparing the dibenzopyrimidoazepines, to morphanthridine derivatives useful as intermediates in the processes for preparing the dibenzopyrimidoazepines and to pharmaceutical preparations containing certain dibenzopyrimidoazepines and morphanthridines.

The novel dibenzopyrimidoazepines of the present invention are compounds of the general formula (I)

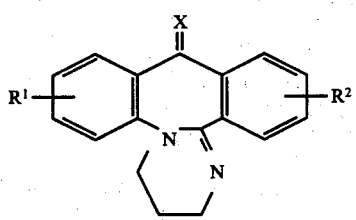

and their acid addition and quaternary ammonium salts. In general formula (I) $R^1$ and $R^2$ each represent hydrogen, lower alkyl, lower alkoxy, halogen or trifluoromethyl and X represents two hydrogen atoms, an oxo group, a protected oxo group or an oximino group.

The term "lower" as used herein means that the radical referred to contains 1 to 6 carbon atoms. Preferably such radicals contain 1 to 4 carbon atoms.

The groups $R^1$ and $R^2$ can be hydrogen, lower alkyl, (e.g. methyl, ethyl, propyl or butyl), lower alkoxy (e.g. methoxy, ethoxy, propoxy or butoxy), trifluoromethyl or halogen such as fluorine, chlorine or bromine. The groups can be the same or different but preferably both $R^1$ and $R^2$ are hydrogen.

X can be two hydrogen atoms

an oxo group (=O), an oximino group (=NOH) or a protected oxo group, for example, a ketalised oxo group such as an alkylene ketal or a di-(lower alkyl) ketal group. The compounds in which X is a protected oxo group are primarily useful as intermediates for preparing the compounds in which X is an oxo group. Compounds in which X represents two hydrogen atoms, an oxo group or an oximino group having pharmacological activity (as described in greater detail below) and hence preferred compounds of the present invention are those of general formula (II)

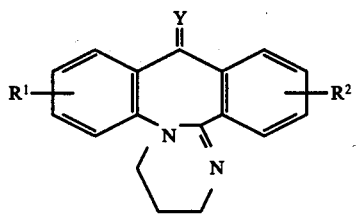

and their pharmaceutically acceptable acid addition and quaternary ammonium salts, wherein $R^1$ and $R^2$ are as defined above and Y represents two hydrogen atoms, an oxo group or an oximino group. Preferred compounds of general formula II are those in which $R^1$ and $R^2$ each represent hydrogen, lower alkyl, lower alkoxy or halogen, especially such compounds in which at least one of the $R^1$ and $R^2$ groups is hydrogen.

A preferred method of preparing the novel dibenzopyrimidoazepines of the present invention comprises cyclising a haloalkylamino-morphanthridine derivative of general formula (III)

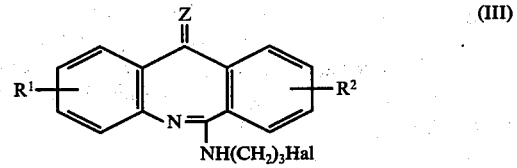

or an acid addition salt thereof, wherein $R^1$ and $R^2$ have the meanings given above, Hal is a halogen atom such as chlorine or bromine and Z is two hydrogen atoms, an oxo group or a protected oxo group, and if desired converting a resulting compound of general formula (I) into another compound of general formula (I) by a known method and/or converting a free base of general formula (I) into an acid addition or quaternary ammonium salt thereof.

The haloalkylamino-morphanthridine may be cyclised by treatment with a base such as alkali metal alkoxide, e.g. sodium methoxide. The haloalkylamino-morphanthridine is preferably dissolved in an inert solvent (e.g. methanol) and heated e.g. at the reflux temperature in the presence of the base.

Once a compound of general formula (I) has been prepared by the cyclisation procedure it may be converted into another compound of general formula(I) by known methods. For example, a compound of general formula (I) in which X is a protected oxo group may be deprotected to give a compound in which X is a oxo group e.g. a compound in which X is a ketalised oxo group may be de-ketalised by hydrolysis. A ketalised oxo group may be hydrolysed by heating with acid e.g. dilute mineral acid or, more preferably, the compound may be hydrolysed by treating the compound with concentrated sulphuric acid at low temperatures (e.g. room temperatures or below, for example, about 0° C).

A compound in which X is an oxo group may be oximated, by treatment with hydroxylamine, to give a compound in which X is an oximino group.

A compound in which X is an oxo group may be reduced to a compound in which X represents two hydrogen atoms and conversely a compound in which X represents two hydrogen atoms may be oxidised to a compound in which X is an oxo group.

A second general method for preparing the dibenzopyrimidoazepines of the present invention comprises cyclodehydrating a hydroxyalkylamino-morphanthridine of general formula (IV)

wherein $R^1$, $R^2$ and Z have the meanings given above, and if desired converting a resulting compound of general formula (I) into another compound of general formula (I) by a known method and/or converting a free base of general formula (I) into an acid addition or quaternary ammonium salt thereof.

The hydroxyalkylamino-morphanthridine of general formula (IV) may be cyclodehydrated by heating it preferably in an inert solvent, at elevated temperatures. The cyclodehydrated compound of general formula (I) can be converted into other compounds of general formula (I) by the methods described above.

A third general method for preparing the novel dibenzopyrimidoazepines of the present invention comprises cyclodehydrating an aminoalkyl-morphanthridine of general formula (V)

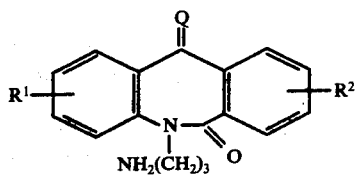

(V)

wherein $R^1$ and $R^2$ have the meanings given above and Q is two hydrogen atoms or a protected, e.g. ketalised, oxo group and if desired converting a resulting compound of general formula (I) into another compound of general formula (I) by a known method and/or converting a free base of general formula (I) into an acid addition or quaternary ammonium salt thereof.

The compound of general formula (V) may be cyclodehydrated to the compound of general formula (I) by heating it, for example, in an inert organic solvent. The solvent can be, for example, o-dichlorobenzene or xylene. The cyclodehydrated compound of general formula (I) can be converted into other compounds of general formula (I) by the methods described above.

The morphanthridines of general formulae (III), (IV) and (V) are novel compounds and are also provided by this invention. Besides being useful as intermediates for preparing the novel dibenzopyrimidoazepines the morphanthridines of general formula (III) and the pharmaceutically acceptable acid addition salts thereof, in which Z is an oxo group, or, preferably, two hydrogen atoms possess hypoglycaemic activity when tested by the pharmacological test procedure given in greater detail hereinbelow.

The haloalkylamino-morphanthridine of general formula (III) may be prepared by treating a hydroxyalkylaminomorphanthridine of general formula (IV) with a hydroxyl/halogen exchange reagent. By "a hydroxyl/halogen exchange reagent" is meant a reagent capable of displacing the hydroxyl group of an alcohol by a halogen atom. Typical examples are phosphorus trichloride, phosphoryl chloride and thionyl chloride. The preferred reagent is thionyl chloride. The reaction is preferably carried out by heating the reagents in an inert solvent (e.g. chloroform). If the product is a compound of formula (III) in which Z is a protected oxo group the group may be de-protected by the methods described above to give a compound in which Z is an oxo group.

The compounds of general formula (IV) may be prepared by reacting a compound of general formula (VI)

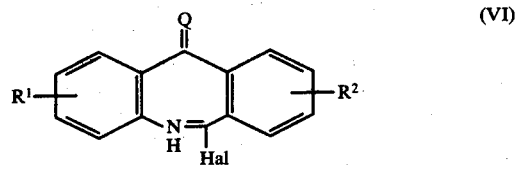

(VI)

where $R^1$, $R^2$, Hal and Q have the meanings given above with 3-aminopropanol and if desired removing the protecting group from a resulting compound of formula (IV) in which Z is a protected oxo group to give a compound of formula (IV) in which Z is an oxo group.

The compounds of general formula (VI) are known or can be prepared by known methods as outlined in the reaction scheme below:-

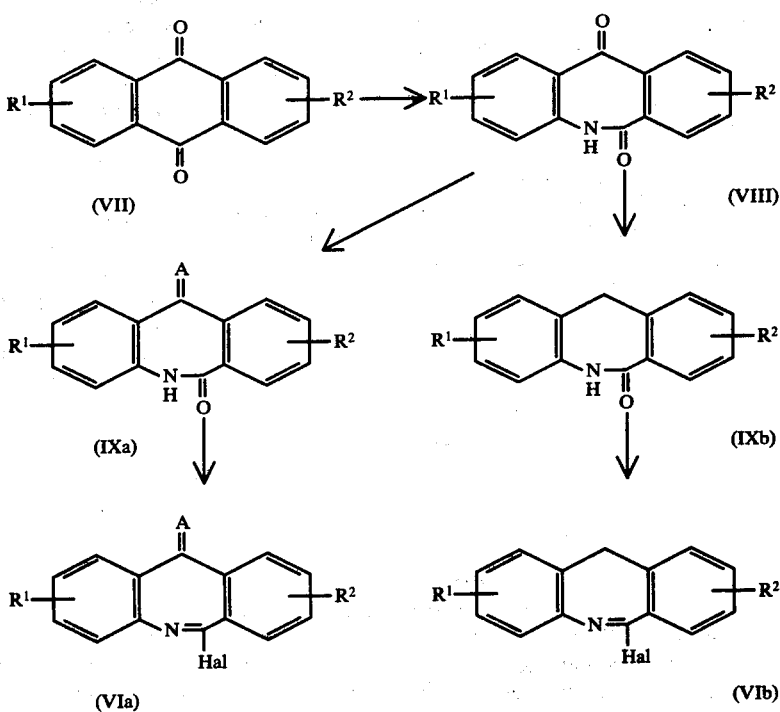

In the reaction scheme R¹, R² and Hal have the meanings given previously and A represents a protected oxo group. According to the reaction scheme an anthraquinone of general formula VII is subjected to a Schmidt reaction (reaction with hydrazoic acid in presence of strong mineral acid, e.g. sodium azide and concentrated sulphuric acid) to give a morphanthridine of general formula (VIII). The 11-oxo group of the latter compound is then protected (e.g. ketalised) to give a compound of formula (IXa) or the compound of formula (VIII) is reduced (e.g. by catalytic hydrogenation) to give a compound of formula (IXb). The compounds of formulae (IXa) or (IXb) are then reacted with a hydroxyl/ halogen exchange reagent (e.g. phosphorus pentachloride) to give compounds (VIa) or (VIb). The aminoalkyl-morphanthridines of general formula (V) may be prepared by hydrogenating a nitrile of general formula (X).

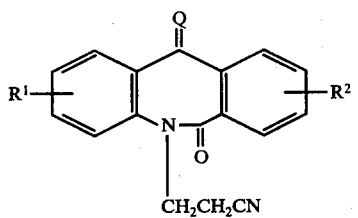

(X)

wherein R¹, R² and Q have the meanings given above. The hydrogenation is usually carried out in the presence of a nickel, palladium or platinum catalyst and at elevated temperatures and pressures. However, if the nitrile contains any substituents which are liable to be affected by drastic hydrogenation conditions, the hydrogenation should be carried out under mild conditions. For example, a suitable Raney nickel can be employed and hydrogenation carried out at relatively low pressures and temperatures.

The nitriles of general formula (X) may be prepared by a Michael addition of acrylonitrile to a compound of general formula (IXa) or (IXb). For example, the compound of general formula (IXa) or (IXb) can be reacted with acrylonitrile in an inert solvent in presence of a basic catalyst. A particularly suitable basic catalyst is benzyltrimethylammonium hydroxide (Triton B).

If in any of the reactions described above a substituent R¹ or R² would interfere with the reaction this substituent should be introduced at a later stage of the synthesis.

The compounds of formula (I) are capable of forming acid addition salts with acids, particularly pharmaceutically acceptable acids and the invention also provides salts. The salts may be isolated directly from the processes described above or prepared by dissolving the specific compound of formula (I) as its base in a suitable organic solvent, and treating it with a solution of the selected acid, in accordance with conventional procedures for preparing acid addition salts from base compounds generally. As examples of acids, there may be used any of hydrochloric, hydrobromic, tartaric, phosphoric, maleic, citric, methanesulphonic or p-toluenesulphonic acids. The compounds of general formula (I) are also capable of forming quaternary ammonium salts, and the invention also provides such salts. The quaternary salts may be prepared by treating the compound as its base in the presence or absence of a solvent, with for example, an aryl-lower alkyl halide, lower alkyl halide, alkenyl halide, alkynyl halide or aminolower alkyl halide. Examples of such halides include methyl iodide and benzyl chloride and benzyl bromide.

The compounds of general formula (II) possess hypoglycaemic activity, as shown by standard tests on warmblooded animals. The compounds can be tested for hypolglycaemic activity by the following procedure:

Male rats weighing 170–200 grams are fasted overnight. A control blood sample is taken from the tail and the sample of test compound is then administered by stomach tube. Subsequent blood samples are taken at hourly intervals for five hours and the change in the blood sugar concentration is determined. In this procedure it was found that representative compounds of formula (II) produced a depression in blood sugar of more than 20% for more than one of the hourly test samples when administered at 50 mg/kg or less.

Examples of such compounds include 10-oximino-3,4-dihydro[2H]dibenzo[c,f]pyrimido[1,2-a]azepine and 3,4-dihydro[2H,10H]dibenzo[c,f]pyrimido [1,2-a]azepine. As mentioned above the morphanthridines of general formula (III) in which Z is oxo group or two hydrogen atoms and their pharmaceutically acid addition salts also possess hypoglycaemic activity. A particularly active compound in the above described test procedure is 6-(3-chloropropylamino)-morphanthridine and its pharmaceutically acceptable acid addition salts. This compound also shows hypotensive activity.

The invention further provides a pharmaceutical composition which comprises a compound of general formula (II) or a pharmaceutically acceptable acid addition or quaternary ammonium salt thereof or a compound of general formula (III) in which Z is an oxo group or two hydrogen atoms or a pharmaceutically acceptable acid addition salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxy-methyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finelydivided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet inself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form. The daily dose of compound will vary depending upon the route of administration, the particular compound employed and the particular animal involved. The daily dose could be, for example, within the range 0.5 to 25 mg/kg depending upon the method of administration and the specific compound.

The follownng Examples illustrate the invention. All temperatures are in ° C.

Example 1

6′-Chlorospiro[1,3-dioxolane-2,11′-morphanthridine]

Phosphorus pentachloride (3.12g., 0.015 mole) was added to a stirred solution of spiro [1,3-dioxolane-2,11′-morphanthridin]6′-one (2.67g., 0.01 mole) in dry benzene (50 ml) and the mixture heated under reflux for 1 hour. After cooling, the solution was filtered, the solvent and phosphoryl chloride removed and the residue recrystallised from toluene/petroleum ether (b.p. 60°-80°) to give the title compound, 1.44g., m.p. 174°-176°. [Found: C, 67.65; H, 4.3; N, 4.85% $C_{16}H_{12}ClNO_2$ requires C, 67.3; H, 4.25; N, 4.9%].

EXAMPLE 2

3-(Spiro[1,3-dioxolane-2,11′-morphanthridin]-6′-ylamino)-1-propanol

A solution of 6′-chlorospiro[1,3-dioxolane-2,11′-morphanthridine] (1.43g., 0.005 mole) and pyridine (0.41 ml., 0.005 mole) in 3-amino-1-propanol (5 ml) was heated at 120° for 24 hours. After cooling, the solution was poured onto water, extracted with dichloromethane and the combined extracts washed twice with water and dried over magnesium sulphate. Removal of the solvent gave a crystalline residue which gave the pure title compound as colourless needles from ethyl acetate, 1.15g., m.p. 172.5°-173.5°. [Found: C, 70.4; H, 6.25; N, 8.5%, $C_{19}H_{20}N_2O_3$ requires C,70.35; H, 6.2; N, 8.65%].

EXAMPLE 3

6′-(3-Chloropropylamino)sprio[1,3-dioxolane-2,11′-morphanthridine]hydrochloride.

Thionyl chloride (1.1 ml., 0.015 mole) was added dropwise to a stirred solution of 3-(spiro[1,3-dioxolane-2,11′-morphanthridine]-6′-ylamino)-1-propanol (1.62 g., 0.005 mole) in dry chloroform (10 ml) and the solution heated under reflux for 2 hours. On dilution with a small volume of ether the title compound cyrstallised, 1.795 g., slow dec. >ca. 180°. [Found: C. 59.9; H, 5.5; N, 7.2%.$C_{19}H_{19}ClN_2O_2$ HCl requires C, 60.15; H, 5.35; N, 7.4%].

EXAMPLE 4

5′, 6′-Dihydro-6′-oxospiro[1,3-dioxolane-2,11′-morphanthridine]-5-propionitrile

Acrylonitrile (7.5 ml) was added dropwise to a stirred, boiling solution of spiro[1,3-dioxolane-2,11′-morphanthridin]-6′-one (6.675g., 0.025 mole) and 'Triton B' (0.5 ml) in dioxan (100 ml), and the solution heated under reflux for a further 90 minutes. After removal of the solvent the residue was eluted through a short column of alumina with chloroform. Removal of the chloroform from the first few fractions gave an oil which crystallised from ethanol/methanol at 0° to give the title compound: 6.12g., m.p. 94°-96°. [Found: C, 70.9; H, 5.0; N, 8.8%. $C_{19}H_{16}N_2O_3$ requires C, 71.25; H, 5.0; N, 8.75%].

EXAMPLE 5

5′-(3-Aminopropyl)spiro[1,3-dioxolane-2,11′-morphanthridin]-6′(5′H)-one

A solution of the nitrile product of Example 4 (8 g.) in absolute ethanol (50 ml.) and ammonia saturated ethanol (100 ml.) was hydrogenated at ca. 1200 p.s.i. over W2 Raney nickel catalyst at 50° for 3 hours. After filtering the solvent was removed, the residue dissolved in benzene, and extracted with dilute hydrochloric acid. The product came out of solution as an insoluble oily hydrochloride. This oil plus the acid extracts were basified with ammonium hydroxide, extracted with chloroform and the combined extracts washed and dried over magnesium sulphate. Removal of the solvent gave the title compound as an oil (6.165 g.). A fumarate salt crystallised from methanol/ethyl acetate, m.p. 160°-163+. [Found: C, 62.75; H, 5.7; N, 6.55%. $C_{19}H_{20}N_2O_3$. $C_4H_4O_4$ requires C, 62.7; H, 5.5; N, 6.35%].

EXAMPLE 6

3,4-Dihydrospiro[dibenzo[c,f]pyrimido[1,2-a]azepine-10(2H), 2′-[1,3]-dioxolane]

a. A solution of 6′-(3-chloropropylamino)spiro[1,3-dioxolane-2,11′-morphanthridine]hydrochloride (1.0 g., 0.005 mole) in methanol (50 ml.) and 5N aqueous sodium hydroxide solution (2.5 ml.) was heated under reflux for 90 minutes. After evaporation of the solvent the residue was diluted with water and extracted with chloroform. The combined extracts were washed, dried over magnesium sulphate and evaporated to give a crystalline residue, recrystallised as colourless needles from ethyl acetate (1.42 g., m.p 182°-183°). [Found: C, 74.4; H, 6.15; N, 9.1%.$C_{19}H_{18}N_2O_2$ requires C, 74.5; H, 5.9; N, 9.15% ]. A hydrobromide salt crystallised from isopropanolether, m.p. 310°-312° dec. [Found: C, 58.95;

H, 5.05; N, 7.15%. $C_{19}H_{18}N_2O_2$ HBr requires C, 58.95; H, 4.95; N, 7.25%.]

b. A solution of 5'-(3-aminopropyl)spiro[1,3-dioxolane-2,11'-morphanthridin]-6'(5'H)-one (1.0g.) in o-dichlorobenzene was heated under reflux with removal of the water formed for 24 hours. After removal of the solvent the residue slowly crystallised from ethyl acetate to give the crude title compound which was crystallised from ethyl acetate.

EXAMPLE 7

3,4-Dihydrodibenzo[c,f]pyrimido[1,2-a]azepin-10(2H)-one 3,4 - Dihydrospiro[dibenzo[c.f]pyrimido[1,2 - a[azepine-10(2H),2'-[1,3]-dioxolane](2.0g.) was added portionwise to vigorously, mechanically stirred concentrated sulphuric acid (10 ml) at 0°. After addition, the mixture was stirred for a further hour at 0° and poured onto ice. The mixture was carefully basified with 0.880 ammonia solution, extracted with dichloromethane and the combined extracts washed and dried over magnesium sulphate. Removal of the solvent yielded an oily mixture which was taken up in hot cyclohexane and filtered from an insoluble residue. After evaporation of the filtrate, the residual oil was dissolved in isopropanol and carefully acidified with concentrated hydrobromic acid. The isopropanol/water were evaporated and the residue crystallised from acetone to give the title compound as the hydrobromide hemihydrate, 2.01 g., m.p slow dec >ca. 150°. [Found: C, 58.1; H, 4.6; N, 7.8%. $C_{17}H_{14}N_2O.HBr.\frac{1}{2} H_2O$ requires C, 58.0; H, 4.6: N, 7.95%].

EXAMPLE 8

10-Oximino-3,4-dihydro[2H]dibenzo[c,f]pyrimido[1,2-a]azepine

A solution of 3,4-dihydrodibenzo[c,f]pyridimo[1,2-a]azepin-10(2H)-one (from basification of 1.056 g., 0.003 mole of hydrobromide salt) and hydroxylamine hydrochloride (0.42 g., 0.006 mole) in pyridine (10 ml.) was heated at 100° for 1 hour. After removal of the solvent the residue was poured onto water and basified with ammonium hydroxide. The precipitate was filtered and recrystallised from methanol/isopropanol, (0.582 g., m.p 260°-265°dec.). A hydrochloride salt crystallised from methanol/chloroform/ether; slow dec.>ca. 250°; solvated with one molecule of methanol. [Found: C, 62.6; H, 6.0; N, 12.3%. $C_{17}H_{15}N_3O$ HCl.CH$_3$OH requires C, 62.5; H, 5.8; N, 12.15%].

EXAMPLE 9

6-(3-Hydroxypropylamino)morphanthridine

To a solution of 6-chloromorphanthridine (10.5g., 0.046 mole) in 3-amino-1-propanol (50 ml.) was added pyridine (7.45 ml., 0.092 mole). The solution was heated for 2 hours at 120°, after which it was cooled, poured on to water, dried, evaporated and triturated with petroleum ether (b.p. 60°-80° ) to give 10.95 g. crude product. This was recrystallised from ethyl acetate to give the title compound (0.21 g.). m.p. 148°-150°. [Found: C, 76.4; H, 7.1; N, 10.5%. $C_{17}H_{18}N_2O$ requires C, 76.7; H, 6.8; N, 10.5%].

EXAMPLE 10

6-(3-Chloropropylamino)morphanthridine

To a solution of 6-(3-hydroxypropylamino)morphanthridine (7.88 g. 0.03 mole) in dry chloroform (60 ml.) at 0° C was added thionyl chloride (6.5ml., 0.089 mole). The solution was warmed to reflux for two hours, cooled and diluted with ether to give a crystalline product, which was filtered off to give the title compound as its hydrochloride (8.74 g.), m.p. 194°-6°. [Found: C, 62.4; H, 5.7; N, 8.5%. $C_{17}H_{17}N_2Cl$. HCl.1/4 H$_2$O requires C, 62.7; H, 5.7; N, 8.6%].

EXAMPLE 11

3,4-Dihydro[2H,10H]dibenzo[c,f]pyrimido[1,2-a]azepine

To a solution of 6-(3-chloropropylamino)morphanthridine (8.15 g., 0.025 mole) in methanol (150 ml.) was added 5N sodium hydroxide (124 ml. 0.062 mole), and the solution refluxed for 2½ hours. The methanol was evaporated off, the residue diluted with water and extracted with chloroform. The extracts were dried, evaporated and the product crystallised from ethyl acetate to give the title compound, m.p. 139°-141°. [Found: C, 82.5; H, 6.6; N, 11.5%. $C_{17}H_{16}N_2$ requires requires C, 82.2; H, 6.5; N, 11.3%].

EXAMPLE 12

3,4-Dihydro-1-methyl-[2H,10H]dibenzo[c,f]pyrimido-[1,2-a]azepinium iodide

To a solution of 3,4-dihydro[2H,10H]dibenzo[c,f]-pyrimido-[1,2-a]azepine (2.0 g., 0.008 mole) in iso-propyl alcohol (40 ml.) was added methyl iodide (1.24 ml., 0.02 mole). The solution was stirred at 80° C for 1¼ hours, then cooled and the resulting white solid filtered to give 2.87 g. of 3,4-dihydro-1-methyl-[2H,10H]dibenzo[c,f]pyrimido[1,2-a]-azepinium iodide, m.p. 214°-217°. [Found: C, 54.05; H, 4.94; N, 6.88%. $C_{18}H_{19}N_2I.\frac{1}{2}H_2O$ requires C, 54.14; H, 5.05; N, 7.02%].

EXAMPLE 13

8'-Chlorospiro[1,3-dioxolane-2,11'-morphanthridine]-6'(5'H)-one

A stirred suspension of 8-chloromorphanthridine-6,11(5H)-dione (J.Med.Chem.1965. 8, 74; 22g) in ethylene glycol (150 ml) is heated with boron trifluoride diethyl etherate (20 ml) at 100° for 16 hours. The resulting liquid is cooled, neutralised with sodium carbonate solution and poured into water (1L). The precipitate is filtered, dried and recrystallized from a suitable solvent to give the title compound.

EXAMPLE 14

6'8'-Dichlorospiro[1,3-dioxolane-2,11'-morphanthridine].

Using a method analogous to that of Example 1, 8' chlorospiro [1,3 - dioxolane - 2,11' - morphanthridin]-6'(5'H)-one is reacted with phosphorus pentachloride in benzene to give the title compound.

EXAMPLE 15

3-(8'-Chloro-spiro[1,3-dioxolane-2,11'-morphanthridin]-6'-ylamino) -1-propanol

Using a method analogous to that of Example 2, 6',8'-dichlorospiro[1,3-dioxolane-2,11'-morphanthridine] is reacted with 3-aminopropanol and pyridine to give the title compound.

EXAMPLE 16

8'-Chloro-6'-(3-chloropropylamino)spiro[1,3-dioxolane-2,11'-morphanthridine]

Using a method analogous to that of Example 3, thionyl chloride is reacted with 3-(8'-chlorospiro[1,3-dioxolane-2,11'-morphanthridin]-6'-ylamino)-1-propanol to give the title compound which may be isolated as its hydrochloride salt.

EXAMPLE 17

13-Chloro-3,4-dihydrospiro[dibenzo(c,f)pyrimido[1,2-a] azepine-10(2H),2'[1,3]-dioxolane]

Using a method analogous to that of Example 6(a), a solution of 8'-chloro-6'[3-chloropropylamino]spiro[1,3-dioxolane-2,11'-morphanthridine] in aqueous methanol is reacted with sodium hydroxide to give the title compound.

EXAMPLE 18

13-Chloro-3,4-dihydrodibenzo[c,f]pyrimido[1,2-a]azepin10(2H)-one

13-Chloro-3,4-dihydrosphior[dibenzo(c,f)pyrimido[1,2-a] azepine-10(2H),2'[1,3]-dioxolane is hydrolysed by a procedure analogous to that of Example 7 to give the title compound.

EXAMPLE 19

3'-Methoxyspiro[1,3-dioxolane-2,11'-morphanthiridin]-6'(5'H)-one

3-Methoxymorphanthridine-6,11(5H)-dione (J.Med. Chem., 1965, 8, 74) is reacted with ethylene glycol and boron trifluoride diethyletherate by a procedure analogous to that of Example 13 to give the title compound.

EXAMPLE 20

6'-Chloro-3'-methoxyspiro[1,3-dioxolane-2,11'-morphanthridine]

Using a method analogous to that of Example 1,3'-methoxyspiro [1,3-dioxolane-2,11'-morphanthridine]-6'(5'H)-one is reacted with phosphorus pentachloride to give the title compound.

EXAMPLE 21

3-(3'-Methoxyspiro[1,3-dioxolane-2,11'-morphanthridin]-6'-ylamino)-1-propanol

Using a method analogous to that of Example 2,6'-chloro 3'1-methoxyspiro[1,3-dioxolane-2,11'-morphanthridine] is reacted with 3-aminopropanol and pyridine to give the title compound.

EXAMPLE 22

6'-(3-Chloropropylamino)-3'-methoxyspiro[1,3-dioxolane-2,11'-morphanthridine]

Using a method analogous to that of Example 3, thionyl chloride is reacted with 3-(3-methoxy-spiro[1,3-dioxolane-2,11'-morphanthridin 6'-ylamino)-1-propanol to give the title compound which may be isolated as its hydrochloride salt.

EXAMPLE 23

3,4-Dihydro-7-methoxyspiro[dibenzo(c,f)pyrimido[1,2-a]azepine-10(2H),2'[1,3]-dioxolane]

Using a method analogous to that of Example 6(a), a solution of 6'-(3-chloropropylamino)-3'-methoxyspiro[1,3-dioxolane-2,11'-morphanthridine] in aqueous methanol is reacted with sodium hydroxide to give the title compound.

EXAMPLE 24

3,4-Dihydro-7-methoxydibenzo[c,f]pyrimido[1,2-a]azepin-10(2H)-one 3,4-Dihydro-7-methoxyspiro[dibenzo(c,f)pyrimido[1,2-a]azepine 10(2H), 2']1,3]-dioxolane is hydrolysed by a procedure analogous to that of Example 7 to give the title compound.

EXAMPLE 25

6-Chloro-8-methylmorphanthridine

8-Methylmorphanthridin-6(5H)-one (J.Med.Chem., 1965,8,74) is reacted with dimethylaniline and phosphorus oxychloride according to the method described in Helv Chim.Acta, 1966,49,1433 to give the title compound,

EXAMPLE 26

6-(3-Hydroxypropylamino)-8-methylmorphanthridine

Using a procedure analogous to that described in Example 9, 6-chloro-8-methylmorphanthridine is reacted with 3-amino-1-propanol to give the title compound.

EXAMPLE 27

6-(3-Chloropropylamino)-8-methylmorphanthridine 6-(3-Hydroxypropylamino)-8-methylmorphanthridine is reacted with thionyl chloride by a procedure analogous to that of Example 10 to give the title compound, which can be isolated as its hydrochloride.

EXAMPLE 28

13-Methyl-3,4-dihydro[2H,10H]dibenzo[c,f]pyrimido [1,2-a]azepine

Using a method analogous to that described in Example 11, a solution of 6-(3-chloropropylamino)-8-methylmorphanthridine in methanol is reacted with sodium hydroxide to give the title compound.

I claim:

1. A dibenzopyrimidoazepine selected from the group consisting of compounds having the formula (I):

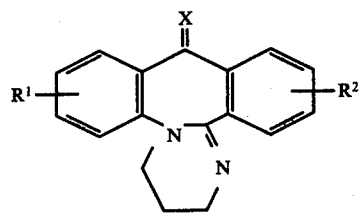

and the pharmaceutically acceptable acid addition and quaternary ammonium salts thereof, wherein $R^1$ and $R_2$ each represent hydrogen, lower alkyl, lower alkoxy, halogen or trifluoromethyl and X represents two hydrogen atoms, an oxo group, an ethylene ketal group, a di-(lower alkyl) ketal group, or an oximino group.

2. A dibenzopyrimidoazepine according to claim 1 of the formula (II)

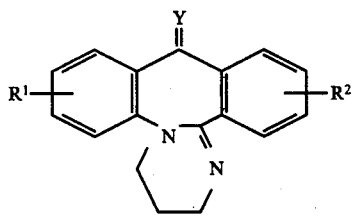 (II)

or a pharmaceutically acceptable acid addition or quaternary ammonium salt thereof wherein R¹ and R² each represent hydrogen, lower alkyl, lower alkoxy, halogen or trifluoromethyl and Y represents two hydrogen atoms, an oxo group or an oximino group.

3. A dibenzopyrimidoazepine according to claim 2 wherein R¹ and R² each represents hydrogen, lower alkyl, lower alkoxy or halogen.

4. A dibenzopyrimidoazepine according to claim 1 which is 3,4-dihydrodibenzo[c,f]pyrimido[1,2-a] azepin-10(2H)-one.

5. a dibenzopyrimidoazepine according to claim 1 which is 10-oximino-3,4-dihydro[2H]dibenzo[c,f]pyrimido[1,2-a]azepine.

6. A dibenzopyrimidoazepine according to claim 1 which is 3,4-dihydro[2H, 10H]dibenzo[c,f]pyrimido [1,2-a]azepine.

* * * * *